United States Patent [19]

Stevens et al.

[11] Patent Number: 4,474,664
[45] Date of Patent: Oct. 2, 1984

[54] ION ANALYSIS METHOD AND APPARATUS

[75] Inventors: Timothy S. Stevens, Midland; James C. Davis, East Lansing; Hamish Small, Midland, all of Mich.

[73] Assignee: The Dow Chemical Company, Midland, Mich.

[21] Appl. No.: 429,357

[22] Filed: Sep. 30, 1982

Related U.S. Application Data

[63] Continuation of Ser. No. 112,579, Jan. 16, 1980, abandoned.

[51] Int. Cl.³ ............................................. G01N 31/04
[52] U.S. Cl. .................................. 210/656; 210/198.2; 436/150
[58] Field of Search ...................... 210/321.1, 638, 656, 210/198.2; 422/70; 436/150

[56] References Cited

U.S. PATENT DOCUMENTS

| | | | |
|---|---|---|---|
| 3,228,876 | 1/1966 | Mahon | 210/22 |
| 3,463,615 | 8/1969 | Sochor | 23/230 |
| 3,751,879 | 8/1973 | Allington | 55/158 |
| 4,187,333 | 2/1980 | Rembaum et al. | 210/321 |

OTHER PUBLICATIONS

Small et al., "Ion Chromatography", 1976, pp. 32-1 to 32-10.
Deelder et al., "Post-Column Reactor Systems in Liquid Chromatography", pp. 669-682, J. of Chromatography, 149 (1978).
Amicon Bulletin CECl On-Line Column Eluate Concentrator, Bulletin I-118G, 6-75.

Primary Examiner—Frank A. Spear, Jr.
Attorney, Agent, or Firm—Burke M. Halldorson

[57] ABSTRACT

A permselective ion-exchange membrane, preferably comprising hollow fiber(s) immersed within a regenerant, is used to selectively neutralize or suppress the conductivity of electrolyte in a stream of eluent also containing chromatographically separated ions. The invention particularly specifies a chromatographic separating column useful with an electrolyte eluent solution to separate ionic species by elution chromatography, wherein the effluent of the separator column is treated by the described membrane to suppress the conductivity of the electrolyte but not that of the separated ions.

32 Claims, 10 Drawing Figures

ION ANALYSIS METHOD AND APPARATUS

This is a continuation of application Ser. No. 112,579, filed Jan. 16, 1980, now abandoned.

FIELD OF THE INVENTION

The invention relates to ion analysis and particularly the field of ion analysis known as ion chromatography.

BACKGROUND OF THE INVENTION

Ion chromatography is a form of commonly practiced ion analysis characterized by the use of two ion-exchange columns in series followed by a flow through conductivity detector. The first column separates the ions of an injected sample by elution of the sample through the column using as the eluent an electrolyte, i.e., usually dilute base or acid in deionized water. The second column, called the "suppressor" or "stripper", functions to suppress the electrical conductivity of the electrolyte in the eluent, but not that of the separated ions such that the latter may be determined by a conductivity cell. The technique is described in more detail in U.S. Pat. Nos. 3,897,213, 3,920,397 3,925,019 and 3,926,559. In addition, various ion-exchange packings useful in the separation column of ion chromatography are described in detail in U.S. Pat. Nos. 3,966,596, 4,101,460 and 4,119,580. A generally thorough description of ion chromatography is additionally given by Small et al., "Proceedings of an International Conference on the Theory and Practice of Ion Exchange", University of Cambridge, U.K., July, 1976; and also, Small et al., "Novel Ion Exchange Chromatographic Method Using Conductimetric Detection", Analytical Chemistry, Vol. 47, No. 11, September, 1975, pp. 1801 et. seq. The foregoing patents and literature publications are fully incorporated herein by reference.

One of the few drawbacks of ion chromatography is that the prior art resin bed type stripper column disadvantageously limits the number of samples which can be consecutively analyzed. As few as five samples, for example, may be run in certain types of analysis before regeneration of the stripper column is required. In addition, low capacity separating resins, e.g., 0.005-0.1 meq/g., and very dilute eluent, e.g., 0.001 to 0.05 molar electrolyte, are necessarily used for prior art ion chromatography, since higher capacity resins and/or higher concentration of electrolyte in the eluent would exhaust the stripper column too rapidly.

The prior art also describes certain difficulties with resin bed stripper columns which are considered to be caused by the variable length of nondepleted resin in the column as it is being used up. It has been observed, for example, that this factor can vary elution times of certain ions, but with less or no effect on other ions. Consequently, the resolution of ions achieved in the separator column can be lost or detrimentally affected in the stripper column. The foregoing literature references by Small et al. supra, and a more recent journal article "Complication in the Determination of Nitrite by Ion Chromatography", Analytical Chemistry, Vol. 51, p. 1571 (1979), discuss in more depth the above and various like complications which can result from technical problems with prior art stripper columns.

It is, accordingly, an objective of this invention to provide improved methods and apparatus for selectively suppressing the electrical conductivity of the electrolyte in the eluent but not the separated ions therein. It is a further objective hereof to provide improved ion chromatography methods and apparatus which allow for continuous analysis of consecutive samples without periodic regeneration or replacement of the stripper column. It is still a further objective of the invention to eliminate unsteady ion responses, i.e., particularly unsteady calibration and elution time variables which are a function of prior art stripper column exhaustion.

THE INVENTION

The invention relates to improved apparatus for ion analysis comprising an eluent reservoir, a chromatographic separating means in communication with said reservoir for receiving eluent therefrom, said separation means comprising a separating medium useful for separating ionic species of a sample eluted therethrough using eluent comprising an electrolyte in solution, suppressor means communicating with said separating means for treating the effluent eluted therefrom, the suppressor means being comprised of a regenerant, and an ion-exchange membrane partitioning said regenerant from the effluent of the separating means, the membrane being preferentially permeable to ions of the same charge as the exchangeable ions of said membrane, the exchangeable ions of said membrane being in the ion form needed to convert said electrolyte of the eluent to a weakly ionized form, and a detector means suitable for detecting resolved ionic species communicating with the suppressor means for receiving the treated effluent therefrom.

A further aspect of the invention is the method of ion analysis comprising eluting a sample of predetermined volume and containing ionic species to be quantitated through a separating medium effective to separate ionic species with the aid of an eluent comprising an electrolyte in solution, thereafter contacting the effluent eluting from the separating medium with an ion-exchange membrane permeable to ions of the same charge as the exchangeable ions of said membrane, and which resists permeation therethrough of ions of the opposite charge, and simultaneously contacting the membrane with a regenerant, said membrane forming a permselective partition between the regenerant and said effluent, whereby ions extracted from the effluent at the active ion-exchange sites of the membrane are diffused through the membrane and are exchanged with ions of said regenerant, and are thus diffused ultimately into said regenerant, the exchangeable ions of the ion-exchange membrane being in that form needed to convert said electrolyte of the eluent to a weakly ionized form, said method including the further step of detecting a resolved ionic species contained in said treated effluent.

The essential feature of the invention is a charged membrane which, e.g., is a strong-base anion-exchange membrane (positively charged) with quaternary ammonium functional groups, and which is most typically in the hydroxide ion form. The invention alternately specifies the use of a charged membrane which is a strong-acid cation exchange membrane (negatively charged) with sulfonic acid functional groups, and which is most typically in the hydrogen (hydronium) ion form. More specifically, such ion-exchange membranes which may be beneficially employed in the practice of the invention are those which are permeable to cations or anions, but not both simultaneously. Thus, the membrane permeates cations, i.e., a cation selective membrane, while resisting permeation of anions, or vice versa. The permeating ions are captured at the active exchange sites of the membrane and thus diffuse through the membrane. The diffusing ions are eventually exchanged near the opposite surface of the membrane with ions from a regenerant and, thus, ultimately diffuse into the regenerant and are thus removed from the analytical stream or separator column effluent. Additionally, the membrane continually replaces the thusly extracted cations or anions with like charged ions which suppress the conductivity of the electrolyte in the eluent. While the membrane is continually being exhausted, it is simultaneously continuously regenerated by the ion-exchange reactions occurring adjacent the interface of the regenerant and the membrane.

Ion-exchange membranes having the permselective ion transfer properties utilized to improve ion chromatography herein are known for other uses in the prior art. For example, ion-exchange membranes of the general type useful herein are described by R. M. Wallace, "Concentration and Separation of Ions by Donnan Membrane Equilibrium," I & EC Process Design and Development, 6 (1967); and are also described for uses such as water softening (U.S. Pat. No. 3,186,941), and the extraction of acids from polymers and metal ions (U.S. Pat. No. 3,244,620 and 3,272,737), all of which are fully herein incorporated by reference.

Although conveniently prepared and employed as a flat sheet, the most preferred practice of the invention utilizes the membrane in the form of a tube, a single hollow fiber or a bundle of hollow fibers. The membrane, depending on its form, is thus fabricated of a film forming, tube forming, or hollow fiber forming polymeric type material which is treated by known sulfonation and/or amination methods to produce the necessary permselective properties. In finished form, the membrane must be formed of a material which, of course, resists dissolution in the various solutions in which it is immersed and/or contacted. It is particularly preferred to form the membrane of polyolefins and most preferably of ethylene polymers, such as polyethylene homopolymer which in ion-exchange form is found to possess excellent solvent resistance and ion transfer properties. The most preferred form of the membrane is the hollow fiber(s) form, and the term "hollow fibers" as used herein means such fibers of less than about 1000 $\mu$ID (internal bore size).

The regenerant may be the same as the regenerants of the prior art, e.g., acid or base dispersed in a fluid most preferably water; and is in preferably flowing contact with the membrane in order to sweep the diffusing ions physically away from the membrane and thus reduce possible leakage back through the membrane. Regenerant is also contemplated comprising immobile acid(s) or base(s), e.g., attached to a polymeric backbone. For example, appropriate ion-exchange resins and particularly such resin partially or completely dissolved in water, or an aqueous slurry of ion-exchange resin, may be used as the regenerant. The latter form of regenerant would be preferred for a static regenerant, for example, that is not designed to be continuously replenished and removed.

The invention has significant advantages over the prior art, for example, it is possible to remove multiple times the usual concentration of electrolyte. In addition, the problems of variable elution times and lack of constant calibration, as heretofore related to various degrees of exhaustion of the prior art resin bed stripper column, appear to be entirely eliminated. In this respect, it would appear that a static or nonchanging ion-exchange front is probably established as opposed to a continually moving or dynamic front suggested to be the kinetics of a resin bed type stripper column. In addition, a better base line control is established since the "carbonate dip" referred to in the prior art is generally stabilized. The ability to operate continuously while eliminating the need for periodic replacement or regeneration of the stripper device, of course, has been long recognized as desirable and is achieved fully by the practice of the present invention.

Additionally, while the improved membrane stripper device of the invention is considered principally as an improvement to be used in lieu of prior art resin bed stripper columns, it is also possible to use a membrane stripper device and resin bed stripper column connected in series in order to achieve extended neutralization capacity, as an illustrative example.

THE DRAWING

Yet further objectives, aspects and advantages of the invention will in part be pointd out in, and in part apparent from, the following more detailed description considered together with the accompanying drawing, in which.

DETAILED DESCRIPTION

Figures 1, 3:
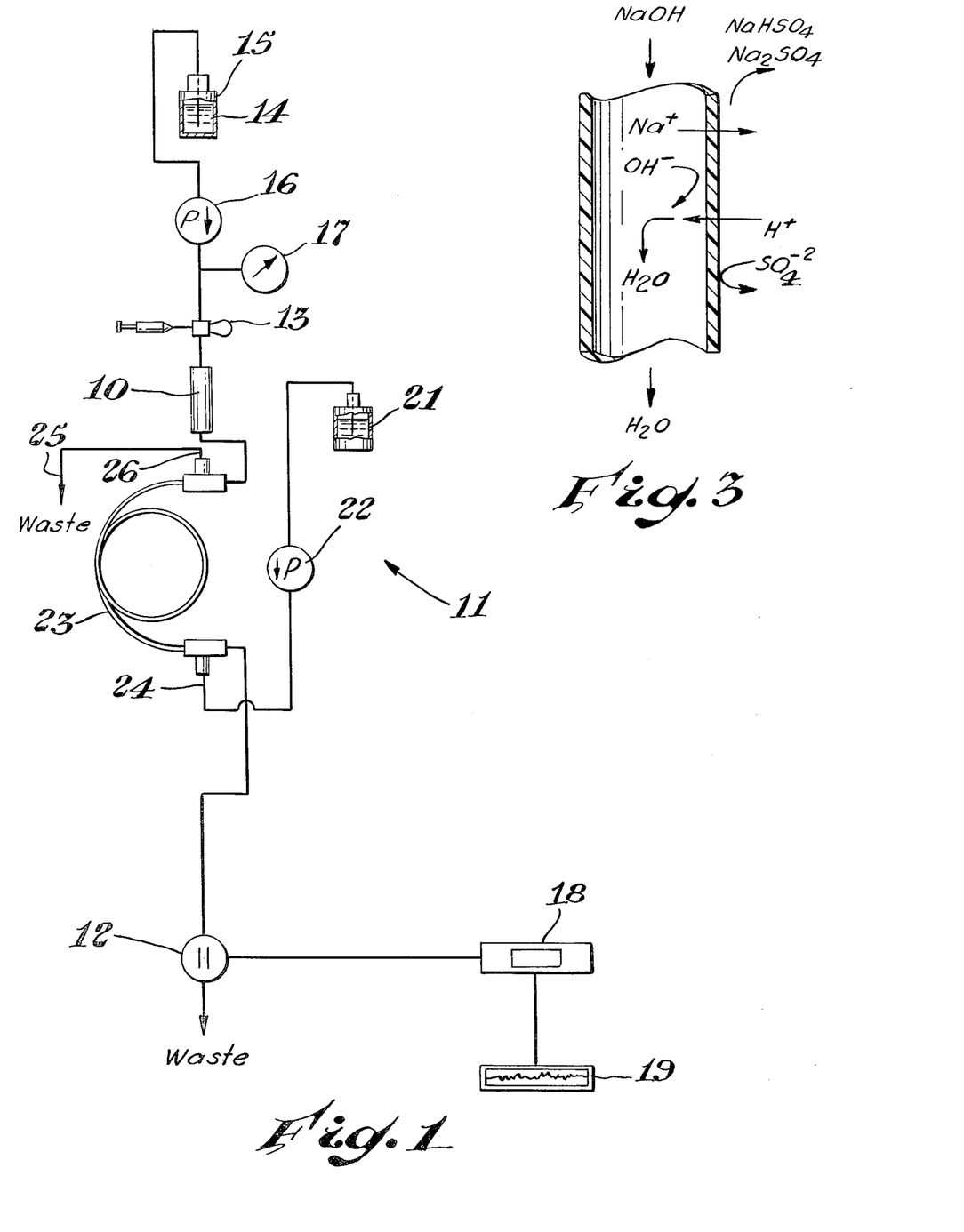
FIG. 1 is an elevational view of apparatus for performing ion chromatography and which is constructed to employ the principles of the invention.
FIG. 3 is an enlarged cross-sectional view of a single hollow fiber membrane, such as may be used in the FIG. 2 device, and graphically illustrates the permselective ion transfer properties of the membrane.

Referring to FIG. 1, there is shown a typical schematic of an ion chromatography instrument or apparatus which is desirably used in practicing the invention, and which comprises a chromatographic separating means comprising a chromatographic column 10 which is packed with an ion exchange separating medium. Most mediums in the art are in the form of ion-exchange resin beds. The invention may employ, however, any form of ion-exchange separating medium useful in separating cations or anions, such as capillary tubes, or such other separating medium as is found or known to be useful to perform ion separations by eluting a sample therethrough using an eluent which contains an electrolyte(s).

Arranged in series with column 10 is a suppressor device or means 11 for suppressing the conductivity of the electrolyte in the eluent, but not the conductivity of the separated ions. This device is particularly described with respect to the detailed description of FIGS. 2 and 3, below.

The suppressing means 11 is followed by a detector suitable for detecting resolved ionic species and preferably a flow-through conductivity cell 12. Sample may be placed on column 10 in most any suitable manner but preferably by means of a syringe added to the system at a sample injection valve 13. The sample injected at valve 13 is swept through the apparatus by a solution of electrolyte, i.e., eluent solution 14 drawn from eluent reservoir 15 by a pump 16, monitored by a pressure gauge 17, and is then passed through the sample injection valve 13 to column 10. Likewise, the eluent solution may be added to column 10 manually as by pouring the solution from a vessel into an open column, but is preferably added in a continuous stream to obtain better uniformity and reproducibility of results. The solution leaving column 10 with the ionic species resolved is conveyed by a liquid conduit to the suppressor means 11 wherein the electrolyte is converted to a weakly ionized form. The solution with resolved species therein is then treated by suppressor means 11 and passed therefrom ultimately to conductivity cell 12.

In the conductivity cell 12 the presence of ionic material produces an electrical signal proportional to the amount of such ionic material and which is directed from conductivity cell 12 to a conductivity meter 18, thus permitting detection of the concentration of separated and conductimetrically responsive species comprising the sample. Processing of the electrical signal is preferably by means of a chart recorder 19 which provides a visible signal, such as for preferred example, in the form of a chromatogram. Additionally, an integrator may be coupled to the chart recorder in order to integrate the area of the peaks generated and shown by the chromatograph, and from which calculation, the concentrations of the various detected ionic species may be determined. The calculation of concentration may also be performed based on peak height as opposed to peak area. Apparatus substantially of the construction described is available commercially from the Dionex Corporation, Sunnyvale, Calif., except for the suppressor means described below, and forming the invention hereof.

The suppressor means 11 is constructed in its most preferred form to include a reservoir or source of regenerant 21, a chromatographic pump 22, and an ion-exchange membrane device 23. There is a conduit means between the reservoir, pump, and membrane device, to deliver regenerant to the latter, the membrane device receiving the regenerant through regenerant inlet 24, and ultimately discharging the spent regenerant to a waste vessel or waste drain 25 via a regenerant outlet 26.

Figure 2:
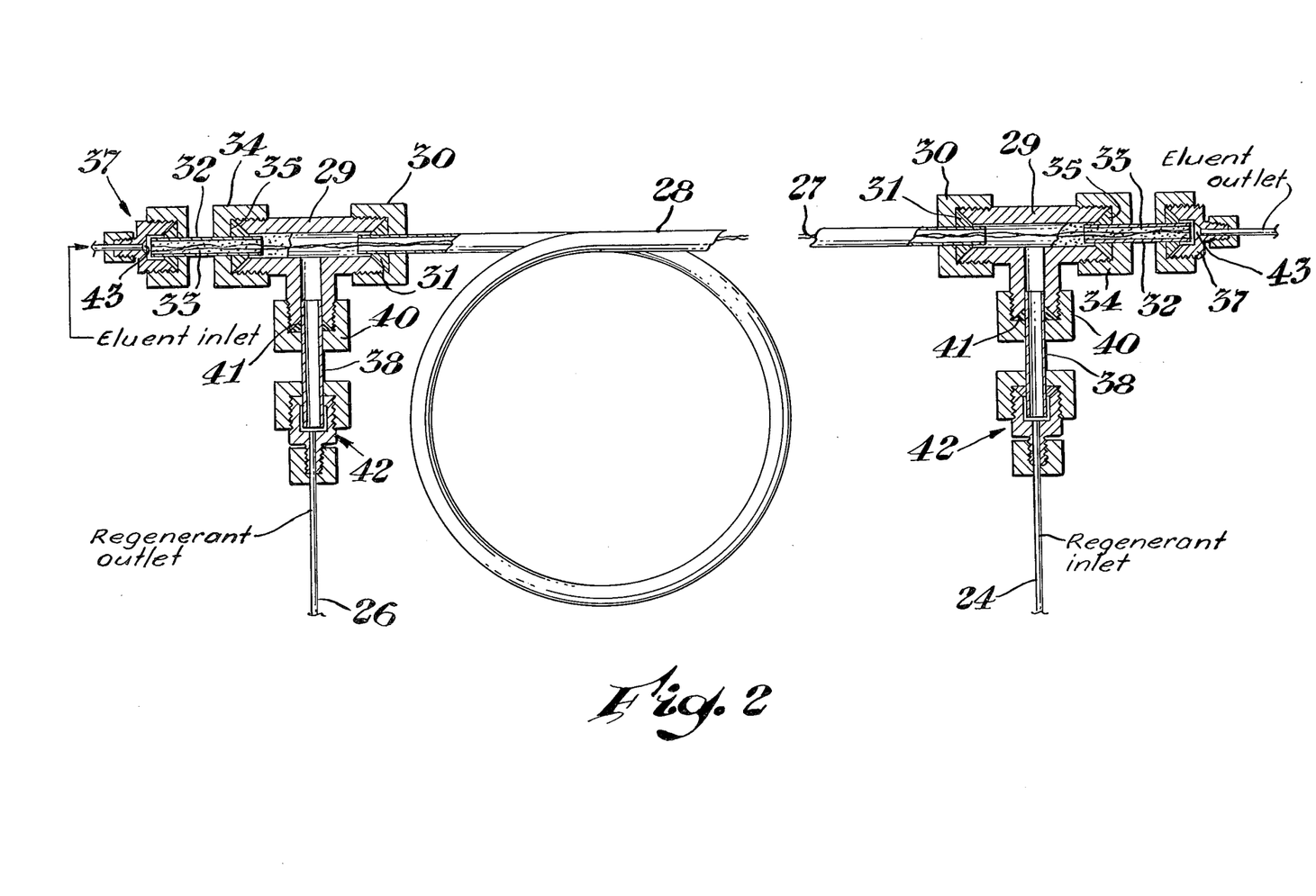
FIG. 2 is a cross-sectional view of the membrane stripper device of the FIG. 1 apparatus.

Referring specifically to FIG. 2, a preferred embodiment of a membrane device 23 is constructed of hollow fibers 27 initially (prior to sulfonation) of 300 $\mu$ID, 380 $\mu$OD, which are sulfonated by a procedure to be described hereinafter, in order to convert the fibers to an H$^+$ form or strong acid ion-exchange material permeable selectively to cations but substantially impermeable or resisting permeation of anions. The fibers are prepared from Product Code No. 4005, low density polyethylene, available commercially from The Dow Chemical Company by extrusion through a spinnette in the known manner.

The device 23 is constructed of a center section of 2 mm ID, $\frac{1}{8}$ inch OD, 316 stainless steel tubing or jacket means 28 through which a bundle of hollow fibers 27 is inserted by suction using water as a lubricant or by gluing the end of a length of thread to a fiber bundle and pulling the fibers through the stainless steel center tubing 28 using water as the lubricant. A tee or tee fitting 29 is affixed to opposite ends, respectively, of center tube 28 using tube nuts 30 with ferrules 31 to make the attachment. The tees used are obtained from Parker Hannifin Corp., Huntsville, Ala. under identifying Part Code No. 2-2-2 JBZ-SS-C.

Exposed portions of the hollow fibers 27 (outwardly of each tee) are dried and inserted into sealing tubes or tube elements 32, respectively, also preferably of stainless steel. A section of about six inches of fibers is left exposed between the sealing tube elements and tees 29 and the exposed fiber sections are coated with a suitable sealant, preferably Silastic 732 RTV silicone rubber (from Dow Corning Corporation, Midland, Mich., as indicated at areas 33, after which the sealing tubes are pushed down and coupled to the tees using tube nuts 34 and ferrules 35. Additional RTV sealant is injected into the sealing tubes using a blunt 20 gauge needle and a 1 cc plastic syringe to completely fill each sealing tube but taking care not to force excess rubber into the tees. The RTV sealant is allowed to cure for 10 minutes to promote bonding of the rubber to the fiber. One end of the exposed fiber bundle is then placed in a beaker of water and suction applied to the other end to draw water through the fibers to swell them. After three days of curing, a razor blade is used to cut the fiber bundle off flush with the end of the sealing tube. The membrane device 23 is then ready to be coupled into the analytical apparatus of FIG. 1. The sealing tubes by means of $\frac{1}{8}$ to 1/16 inch reducing union assemblies 37, preferably Part No. 212-1-HBZ-SS-C from Parker Hannifin Corp., are connected into the section of the conduit means between separating column 10 and conductivity cell 12. The commercial union assemblies are desirably modified by chamfering the small bore of each fitting 37 with a standard 150 inch twist drill, as shown at areas 43, respectively, to avoid possible flow blockage adjacent the fiber ends. The tees 29 define further points of attachment for connection to regenerate inlet 24, and regenerant outlet 26. These latter connections may be of the same type described, supra, using a tube element 38 joined at one end to tees 29 through tube nuts 40 and ferrules 41; and at the opposite end joined respectively to the regenerant inlet and outlet through $\frac{1}{8}$ to 1/16 inch reducing union assemblies 42, preferably of the same type as previously indicated. The device 23 as assembled defines contiguous flow channels comprising, respectively, the collective bores of fibers 27, and the spaces exterior of the fibers within jacket means 28, and which communicate, respectively, with separator column 10 and regenerant reservoir 21.

The suppressor means operates by receiving the effluent of the separator column which is thus routed internally through the hollow fibers 27. Simultaneously, solution from reservoir 21 is pumped in counter flowing fashion into regenerant inlet 24 and removed through regenerant outlet 26 to waste 25, thus making ion-exchanging contact with the exterior surface of the hollow fibers, which internally, are in simultaneous ion exchanging contact with said effluent of the separator column means. The electrolyte component of the eluent is thus neutralized by an ion-exchange reaction with the fiber wall, and the fiber wall is continuously regenerated by the counter flowing regenerant. Passage of excess regenerant into the eluent flow is significantly minimized because of Donnan Exclusion forces, as is passage of the sample ions from the eluent stream to the regenerant stream.

FIG. 3 provides a graphic illustration of the workings of the invention using for illustrative purposes, dilute $H_2SO_4$ in water as the regenerant and NaOH as the electrolyte of the eluent. The ion-exchange membrane partition or partition means, which may be a sulfonated polyethylene hollow fiber(s), allows sodium ion to permeate out and hydrogen ion to permeate in. Hydroxide and sulfate ions tend not to permeate the fiber wall because of Donnan Exclusion forces. Thus, the NaOH stream is converted to deionized water and the Na+ ions permeate the wall of the membrane and are dispersed in the regenerant and thus ultimately routed to waste line 26 as $NaHSO_4$ and $Na_2SO_4$.

If the flow rate of the electrolyte through the fiber is too fast, the time for the ions to diffuse from the center of the fiber bore to the wall of the fiber may be too short for complete neutralization to occur at the desired eluent pumping rate. Accordingly, the use of small internal diameter fibers, in the form of a fiber bundle, would be preferred, or the problem can be minimized by selecting longer fiber(s).

If the fiber wall is too impermeable, incomplete neutralization may also occur. This problem may be overcome by using fibers with a higher level of sulfonation, and thus, greater permeability. Generally also, the meq/min of electrolyte into the device must be matched by at least as many meq/min of regenerant flowing preferably countercurrent about the outside of the fibers. Some excess of regenerant is usually required due to less then 100% efficiency. For example, in the membrane devices tested, below, about 10–50% excess of regenerant on a meq/min of electrolyte is found to work satisfactorily. In addition, Donnan Exclusion forces may not totally block "leakage" of regenerant into the analytical stream, for example, at relatively high regenerant concentrations, or when using a more permeable membrane. Also, weak acid or base ions might be expected to permeate the membrane, thus losing a portion of the sample ions. These factors are studied in some depth below.

EXAMPLE SERIES 1

Several different hollow fiber membrane devices are constructed for experimental testing and comparison using the low density polyethylene fibers described above. Such fibers are sulfonated by a procedure wherein the fibers are coiled in about 3″ diameter coils and secured by Teflon tape. The fibers are subsequently filled with methylene chloride using a gentle vacuum applied to one end of the coil, with the other end dipped in the methylene chloride solution. 250 ml of a 10% solution (v/v) of chlorosulfonic acid in methylene chloride is then placed in a 3 neck/one liter flask equipped with a condenser and a heating mantle. The coiled fibers are placed in the flask and soaked for about 178 hour. The heating mantle is then turned on and the solution heated to the reflux condition. During each 5-minute interval, a glass stirring rod is inserted into the flask to immerse the coil. After sulfonation times varying from 15 minutes to two hours, the fibers are retrieved and placed in 250 ml of methylene chloride to soak for about 178 hour. The fibers are then soaked in deionized water for 24 hours, after which the deionized water is replaced and the soaking step repeated. The finished fibers are then made into the suppressor devices as further characterized in Table I, below:

TABLE I

DESCRIPTION OF THE DEVICES

| Device # | Sulfonation Time of the Fibers (Min) | Capacity of the Fibers meq/g | OD of the Fibers μ | ID of the Fibers μ | Length of Device cm | # of Fibers in Device | Residence Time in Device min | Total Area of Exchanger in Device cm² |
|---|---|---|---|---|---|---|---|---|
| 1 | 15 | 0.5[a] | 420 | 330 | 97 | 12 | 0.93[b] | 120 |
| 2 | 30 | 1[a] | 420 | 330 | 97 | 12 | 0.93[b] | 120 |
| 3 | 60 | 1.95 | 460 | 360 | 81 | 7 | 0.54[b] | 64 |
| 4 | 120 | 4[a] | 540 | 425 | 54 | 5 | 0.36[b] | 36 |

[a] estimated capacity based on the determined capacity of the fibers used in Device #3, in the terms of meq of cation exchange capacity/g of dry sulfonated fiber, assuming a linear relationship between capacity and sulfonation time.
[b] at a flow rate of 64 ml/hr.

EXAMPLE SERIES 2

The effect of regenerant acid "leakage" for different concentrations of nitric acid, phosphoric acid and sulfuric acid regenerant solution is determined using device #3. The eluent is deionized water at flow rate of 64 ml/hr and the regenerant flow rate is 92 ml/hr. Leakage is determined as an increase in conductivity over deionized water. The results in μmho/cm are shown in Table II.

TABLE II

REGENERANT LEAKAGE AS A FUNCTION OF REGENERANT TYPE AND CONCENTRATION
Increase in Conductivity in μmho/cm of Eluent Deionized Water at a Flow Rate of 64 ml/hr

| | Concentration | | |
| Regenerant | 0.01 N | 0.02 N | 0.05 N |
|---|---|---|---|
| $H_3PO_4$ | 22 | — | 160 |
| $HNO_3$ | 12 | — | 200 |
| $H_2SO_4$ | 1.5 | 3 | 12 |

The lower leakage of sulfuric acid shown in Table II is considered due to its high acid strength and the polyvalent nature of the sulfate anion. Polyvalent anions carry a higher charge density that results in a higher repulsion between the fiber wall and the anion. Phosphoric acid is not strong enough to prevent the formation of $H_2PO_4^-$ ions.

EXAMPLE SERIES 3

The effect of leakage as a function of fiber capacity is also studied using an eluent of deionized water at a flow rate of 64 ml/hr, a regenerant flow rate of 92 ml/hr of 0.01N $H_2SO_4$ and 0.05N $H_2SO_4$, and measuring the conductivity of the effluent eluent of each device, the results being reported below:

TABLE III

LEAKAGE COMPARISON OF THE DEVICES
Increase in Conductivity, in μmho/cm, of Eluent Deionized Water at a Flow Rate of 64 ml/hr Using a Regenerant of:

| Device # | 0.01 N $H_2SO_4$ | 0.05 N $H_2SO_4$ |
|---|---|---|
| 1 | ND | 4 |
| 2 | ND | 10 |
| 3 | 1.5 | 24 |

TABLE III-continued

LEAKAGE COMPARISON OF THE DEVICES
Increase in Conductivity, in μmho/cm,
of Eluent Deionized Water at a Flow
Rate of 64 ml/hr Using a Regenerant of:

| Device # | 0.01 N $H_2SO_4$ | 0.05 N $H_2SO_4$ |
|---|---|---|
| 4 | 3 | 70 |

ND = not detected, detection limit 0.5 μmho/cm

The data in Table III indicate that lower capacity fibers have acceptable leakage characteristics since the normal eluents used for anion analysis in ion chromatography have a sodium concentration of about 0.01N allowing hollow fiber stripper regenerant acid concentrations of about 0.02N at similar flow rates as the eluent flow rate. However, low capacity fibers also have a greater resistance to the diffusion of ions through the fiber wall.

EXAMPLE SERIES 4

The dominant factors involved in the resistance to mass transfer of ions in the hollow fiber stripper are assumed to be diffusion through the eluent flow stream to the fiber wall, and then through the fiber wall itself. Two experiments are run in an attempt to show each effect. The first experiment involves the neutralization of a relatively strong eluent, 0.1M naOH, to determine the number of meq/hr of NaOH that can be completely neutralized by a 50% excess countercurrent flow of dilute $H_2SO_4$ for each $cm^2$ of available fiber surface, i.e., diffusional resistance through the fiber wall, and these results are shown in Table IV. The second experiment involves the neutralization of a normal strength eluent, 0.01M NaOH, to determine the maximum rate allowable with complete neutralization by a 50% excess countercurrent flow of dilute $H_2SO_4$. Conditions are chosen where diffusional resistance through the eluent flow stream to the fiber wall are predominant, and this data is shown in Table V.

TABLE IV

EXPERIMENT DESIGNED TO DETERMINE DIFFUSIONAL RESISTANCE THROUGH THE FIBER WALL

| Device # | Maximum flow rate of 0.1 M NaOH with Complete Neutralization | Meq of NaOH neutralized per $cm^2$ of surface area per hour | Residence Time in device at the maximum eluent flow rate |
|---|---|---|---|
| 1 | 32 ml/hr | 0.027 | 1.86 min |
| 2 | 96 ml/hr | 0.080 | 0.62 min |
| 3 | 80 ml/hr | 0.13 | 0.43 min |
| " | 16 ml/hr (1 M NaOH) | 0.25 | 2.16 min |
| 4 | 48 ml/hr | 0.13 | 0.48 min |

TABLE V

EXPERIMENT DESIGNED TO DETERMINE DIFFUSIONAL RESISTANCE TO THE FIBER WALL

| Device # | Maximum flow rate of 0.1 M NaOH with complete neutralization | Meq of NaOH neutralized per $cm^2$ of surface area per hour | Residence Time in device at the maximum eluent flow rate |
|---|---|---|---|
| 1 | 64 ml/hr | 0.0053 | 0.93 min |
| 2 | 96 ml/hr | 0.0080 | 0.62 min |
| 3 | 96 ml/hr | 0.015 | 0.36 min |
| 4 | 64 ml/hr | 0.018 | 0.36 min |

The data in Tables IV and V indicate that the diffusional resistance through the eluent flow stream is predominant under the conditions studied for Devices 2, 3, and 4, e.g., reducing the NaOH concentration of the eluent 10 times allows no increase or only a small increase in flow rate. Only for Device #1 is a significant difference noted between the experiments with regard to maximum eluent flow rate.

Comparing the data regarding leakage in Table III with the diffusional resistance data in Tables IV and V, optimum performance is indicated using fibers of about 1 meq/g capacity (fibers sulfonated as described for 30 minutes as used in Device #2) to minimize regenerant leakage without significant diffusional resistance through the fiber walls using normal eluent strengths (about 0.01N).

EXAMPLE SERIES 5

Based on the comparative results of the preceding Example Series, a membrane device is constructed containing 8 fibers sulfonated as described for 30 minutes, being six feet in length and which is coiled for compactness.

Two prior art stripper columns are compared to this hollow fiber stripper. The first is 2.8 mm×300 mm containing about 1.8 ml of resin. This is a "small" stripper column having a lifetime under typical conditions of about six hours. Small stripper columns are preferred when the ion exclusion effects of stripper column exhaustion need to be minimized. The second prior art stripper column tested is 9 mm×110 mm containing about 7 ml of resin. This "big stripper" has a lifetime of about 24 hours and is used where long column life is more important than reducing the ion exclusion effects in the unexhausted fraction of the stripper column.

Figure 4:
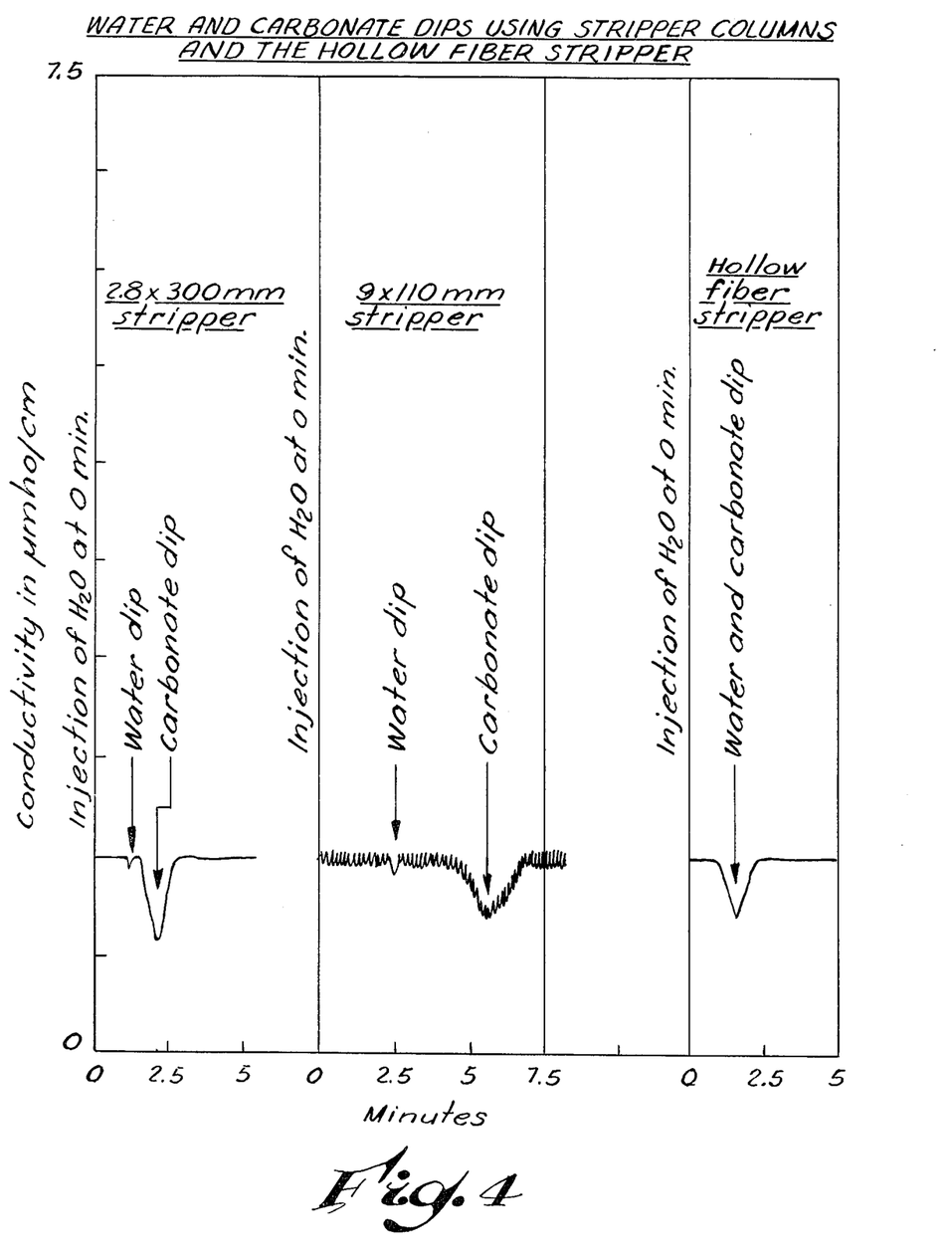
FIGS. 4–10 are chromatograms together with certain graphs developed using the apparatus and method of the invention and/or developed using comparative prior art, and are particularly associated with the Example Series 1–10, below.

The most common eluent used for the determination of anions in ion chromatogaphy contains 0.003M $NaHCO_3$ and 0.0024M $Na_2CO_3$ in deionized water (which is used for the following examples at a flow rate of 64 ml/hr). The stripper converts these eluent electrolytes to carbonic acid which has little conductivity because of its weak acid character. When an injection of deionized water containing no anions is made, two negative peaks are seen in the chromatogram. The first, called the "water dip" is related to the plug of injected water moving through the system with eluent of slightly higher conductivity on either side of it. The second, called the "carbonate dip," is larger and is the vacancy chromatogram for the carbonate not in the injected sample but present in the eluent. That is, carbonic acid elutes through the unexhausted portion of the stripper column at a reduced rate because of ion exclusion effects. When an injection of deionized water is made, the vacancy of carbonate ions elutes through the system at the same rate as an injection of carbonate ions would and a vacancy dip is thus seen. FIG. 4 compares the water dip and the carbonate dip for two freshly regenerated stripped columns and for the hollow fiber stripper.

Also, from FIG. 4, it should be noted that the baseline for the 9×110 mm stripper is unsteady because it has not "aged." Large strippers require many hours of rinsing after regeneration, depending on the batch of resin used, to wash out leachables and this column ultimately gave a steady baseline the following day. Note that the larger stripper's water dip comes later due to increased void volume, and that the separation between the water dip and the carbonate dip is much greater for the larger stripper because of increased ion exclusion effects. Finally, both dips are combined in the hollow fiber stripper because of the apparent absence of ion exclusion effects.

EXAMPLE SERIES 6

Figure 5:
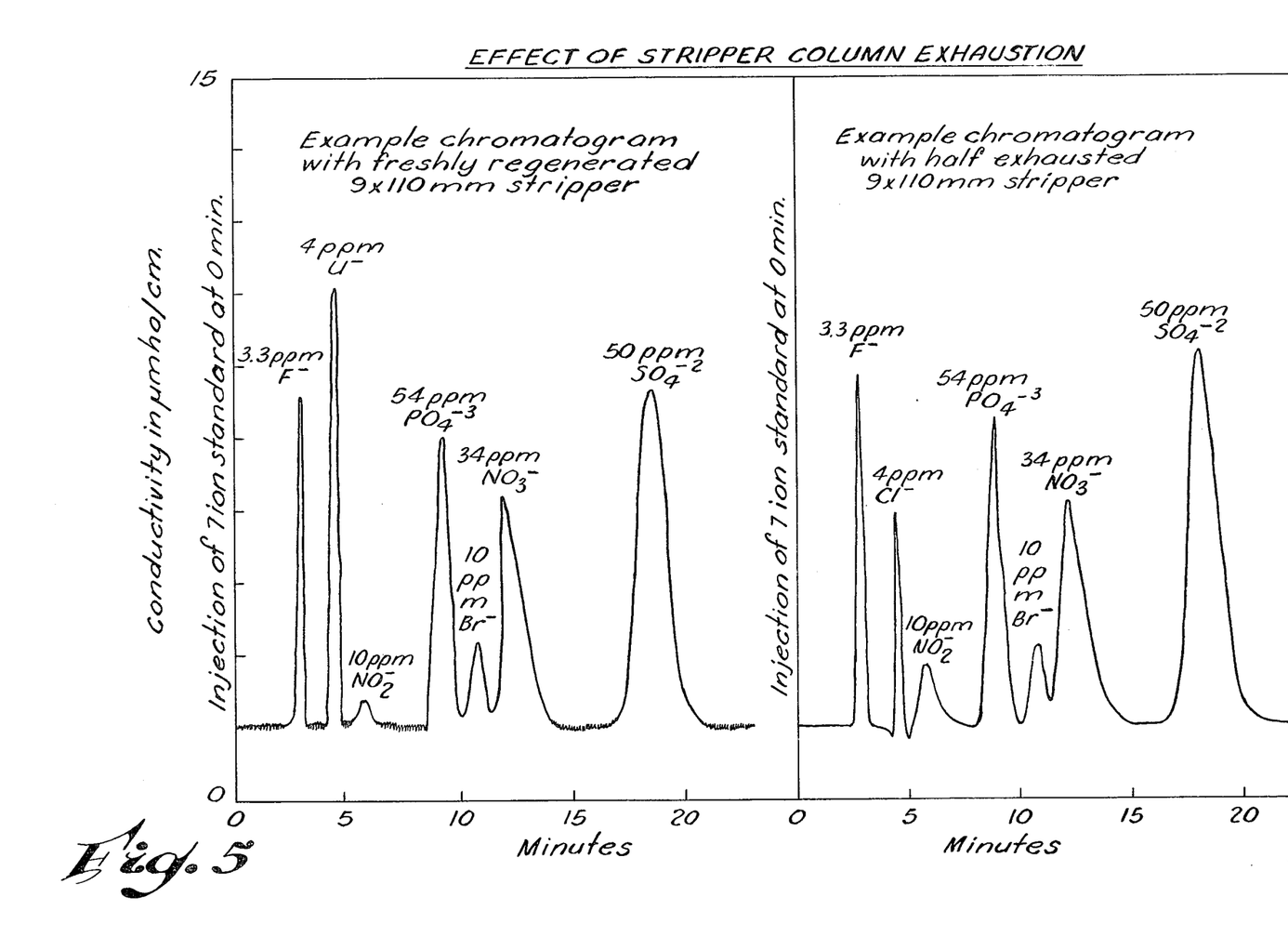

FIG. 5 relates to prior art comparative chromatograms and shows the variance of the elution time of the carbonate dip as a function of column exhaustion. This effect which can produce undesirable variance in the response factor of ions co-eluting with the variable carbonate dip, is shown with respect to an injection of a mixture of seven anions. The position of the carbonate dip is shown specifically at the left of FIG. 5 with respect to a freshly regenerated 9×110 mm prior art stripper, and on the right when the same stripper is about half exhausted. Thus, in the chromatogram on the left, the carbonate dip elutes at about six minutes, co-eluting with $NO_2^-$. In the second chromatogram (at the right), the carbonate dip elutes at about four minutes, co-eluting with $Cl^-$, resulting in a larger response for $NO_2^-$ and a smaller response for $Cl^-$.

Figure 6:
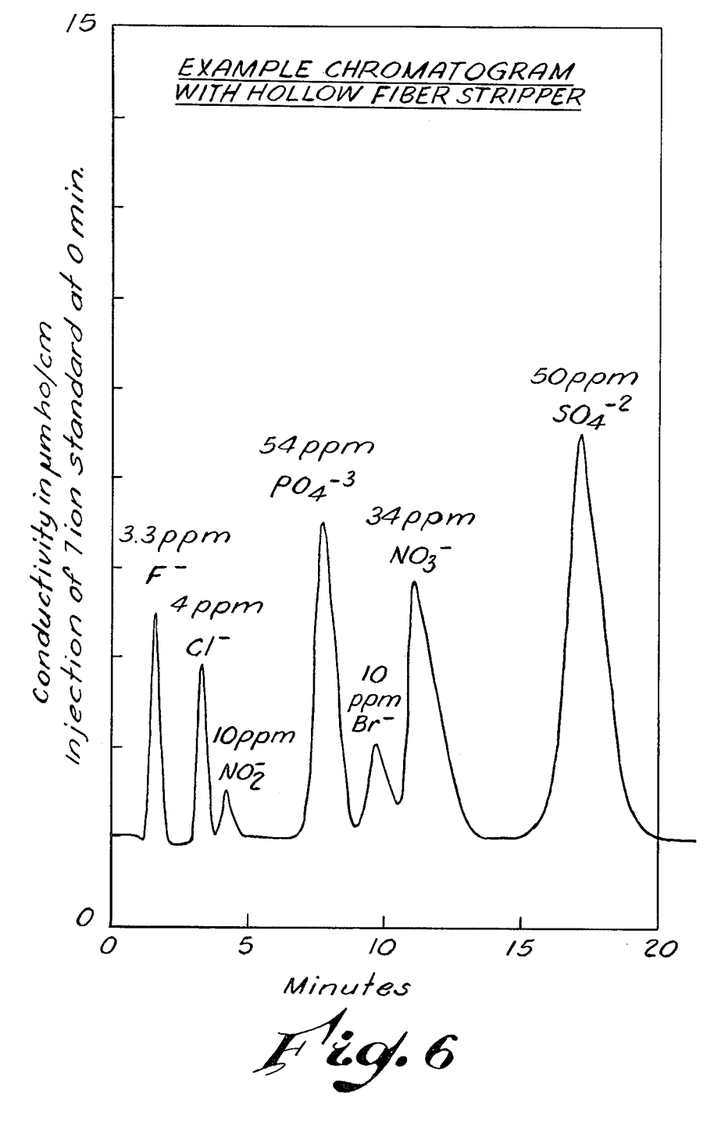

In respect to the invention, FIG. 6 comparatively shows a chromatogram of the same seven ion standard, and which is developed using the hollow fiber stripper. The carbonate dip co-elutes with $F^-$ but its effect can be coped with because it is constant since the hollow fiber stripper does not exhaust with use.

EXAMPLE SERIES 7

The band spreading of each stripper is quantitated by removing the separator column from the system, changing the eluent to deionized water, and injecting a 1:1 dilution of the seven ion standard in deionized water at a detector sensitivity of 120 μmho/cm full scale. The resulting on-scale peak is then triangulated and the peak width at baseline measured and converted to μl. The injection volume is then subtracted from this value, and the results are used as an indication of the band spreading of the system.

TABLE VI

| BAND SPREADING OF THE STRIPPERS | |
|---|---|
| Stripper | Band Spreading |
| 2.8 × 300 mm Packed Column | 130 μl |
| 9 × 110 mm Packed Column | 300 μl |
| Hollow Fiber Stripper | 525 μl |

The data in Table VI indicate that the use of the hollow fiber stripper results in more band spreading than a resin bed stripper column, but in all cases, the strippers tested are satisfactory for use in ion chromatography. Because of variable ion exclusion effects, extended band spreading, however, would be anticipated for the resin bed type strippers with respect to weak anions and cations such as the acetate anion of this Example Series 8, below.

EXAMPLE SERIES 8

Figure 7:
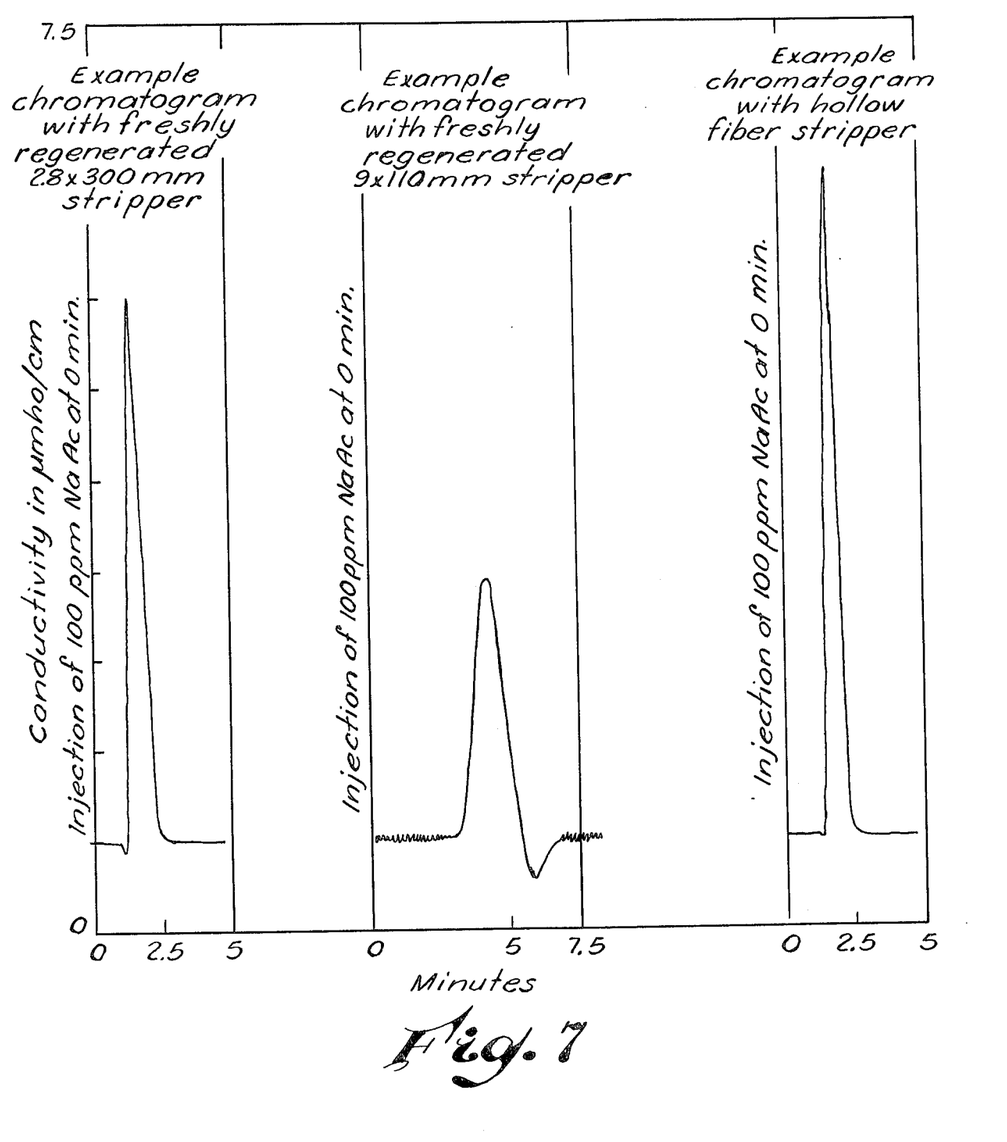

The determination of weak acid anions, such as acetate, using a stripper column, is complicated by ion exclusion effects in the unexhausted portion of the stripper column. FIG. 7 shows chromatograms for the injection of a NaAc standard using the 2.8×300 mm stripper, the 9×110 mm stripper, and the hollow fiber stripper. Expectedly, both resin bed stripper columns, and especially the 9×110 mm stripper, broaden and retard the acetate peak due to ion exclusion effects. The use of the hollow fiber stripper theoretically should have resulted in the loss of the acetate response (and there may indeed be some loss) since protonated acetate is not rejected from passage through the fiber wall. However, FIG. 7 clearly demonstrates the surprising utility of acetate determination using a hollow fiber stripper.

EXAMPLE SERIES 9

Figure 8:
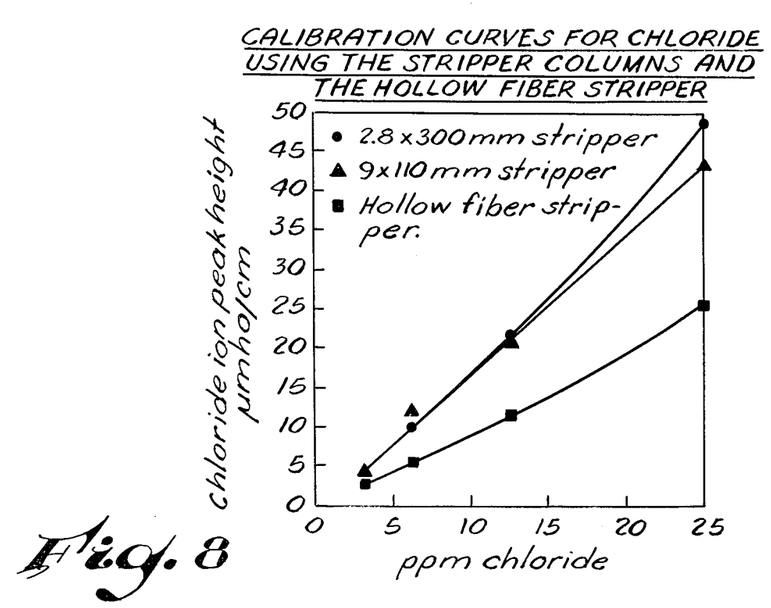
Figure 9:
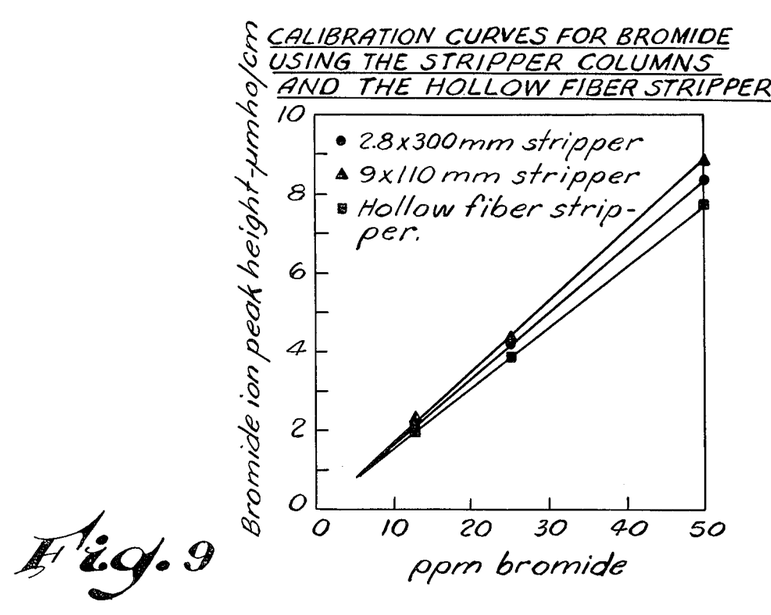
Figure 10:
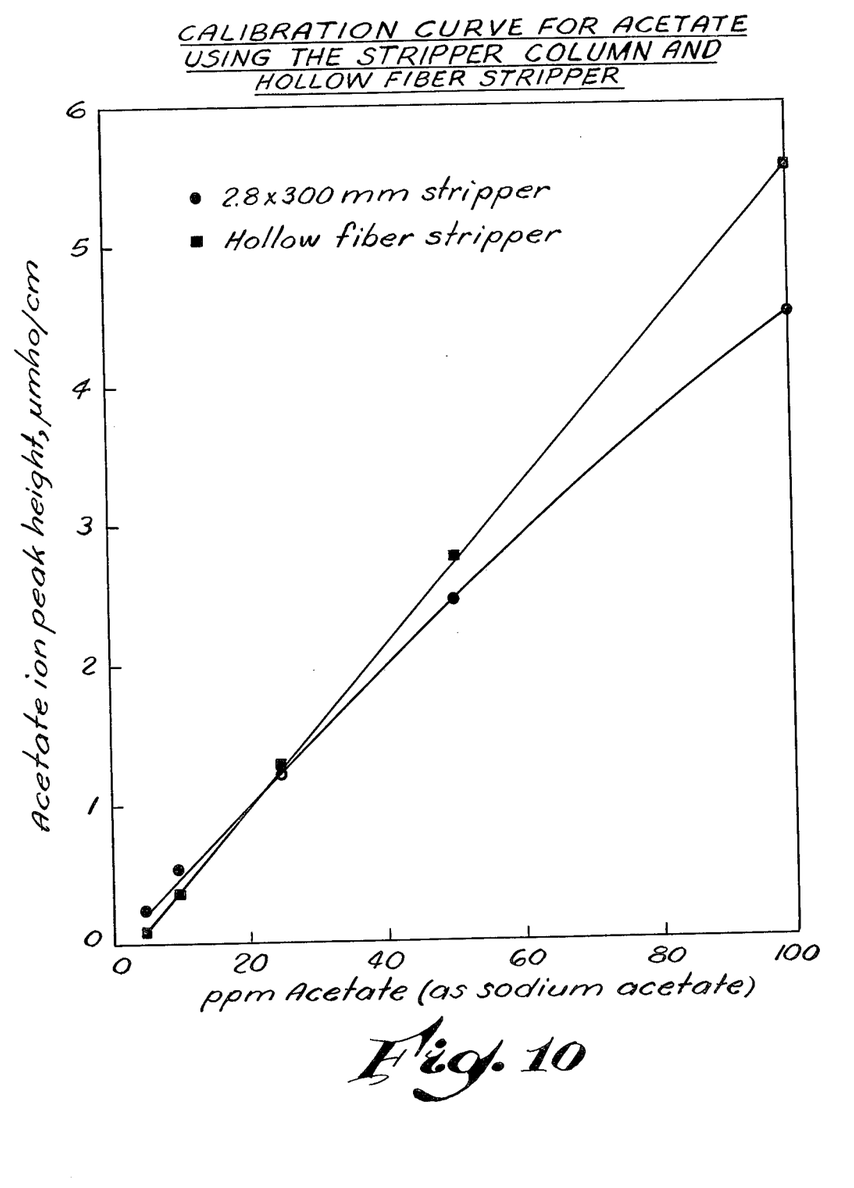

Comparisons made between the stripper columns and the hollow fiber stripper to determine response linearity for chloride, bromide and acetate are shown in the drawing, FIGS. 8–10, respectively.

The data in FIG. 8 indicate that the use of both the 2.8×300 mm and hollow fiber stripper results in increased response with increasing concentration of chloride. The linearity with the 9×110 mm stripper is good. The reduced response with the hollow fiber stripper is caused by the broader chloride peak as a result of band spreading in the hollow fiber stripper. Although the linearity of the 9×110 mm stripper is initially good, the data in FIG. 5 indicates that as the 9×110 mm stripper exhausts and the carbonate dip begins to co-elute with chloride, the responsiveness of chloride would change detrimentally and significantly.

The data in FIG. 9 indicate that the use of any of the strippers tested would result in linear response with respect to bromide. The data in FIG. 10 indicate that the responsiveness of acetate falls off at higher concentration with the use of the 2.8×300 mm stripper, and thus significantly better linearity is shown by the hollow fiber stripper with this type of weak anion analysis. Such linear responsiveness with the use of the hollow fiber stripper at the higher concentrations of acetate is fortunate but cannot be readily explained.

EXAMPLE SERIES 10

Another comparison that is salient to the considerations of the improvements of the hollow fiber stripper is to inject the seven ion standard and the acetate standard periodically during the lifetime of a 2.8×300 mm prior art "small" stripper column, and also conduct the same tests with the hollow fiber stripper. The data should show tendencies for response deviations as a function of time and is set out with respect to the prior art in Table VII, and with respect to the hollow fiber stripper in Table VIII.

TABLE VII

RESPONSE VARIATIONS OBSERVED DURING THE LIFETIME OF THE 2.8 × 300 mm STRIPPER COLUMN

| Ambient Temp. °C. | Elapsed Time Since Regeneration in Hours | PEAK HEIGHT IN CHART UNITS FOR: | | | | | | | |
|---|---|---|---|---|---|---|---|---|---|
| | | $F^-$ | $Cl^-$ | $NO_2^-$ | $PO_4^{-3}$ | $Br^-$ | $NO_3^-$ | $SO_4^{-2}$ | $Ac^-$ |
| 22.0 | 0.3 | 77.0 | 28.7 | 10.5 | 34.0 | 9.5 | 26.0 | 53.0 | — |
| 22.0 | 0.7 | — | — | — | — | — | — | — | 29.8 |
| 22.0 | 0.8 | 75.0 | 29.0 | 10.0 | 33.5 | 9.2 | 25.0 | 37.8 | — |
| 22.0 | 1.5 | 76.2 | 31.0 | 12.0 | 34.5 | 9.5 | 26.5 | 45.0 | — |

TABLE VII-continued
RESPONSE VARIATIONS OBSERVED DURING THE LIFETIME OF THE 2.8 × 300 mm STRIPPER COLUMN

| Ambient Temp. °C. | Elapsed Time Since Regeneration in Hours | PEAK HEIGHT IN CHART UNITS FOR: | | | | | | |
|---|---|---|---|---|---|---|---|---|
| | | F⁻ | Cl⁻ | NO₂⁻ | PO₄⁻³ | Br⁻ | NO₃⁻ | SO₄⁻² | Ac⁻ |
| 22.0 | 2.5 | — | — | — | — | — | — | — | 34.0 |
| 22.0 | 3.2 | 77.0 | 32.5 | 17.0 | 35.5 | 10.2 | 27.5 | 47.2 | — |
| 22.0 | 4.1 | 78.8 | 32.0 | 18.8 | 35.5 | 10.2 | 27.2 | 43.0 | — |
| 22.0 | 5.1 | 79.0 | 31.0 | 22.2 | 35.7 | 10.0 | 27.2 | 40.5 | — |
| 22.0 | 5.5 | — | — | — | — | — | — | — | 51.0 |
| 22.5 | 6.2 | 79.0 | 32.0 | 27.2 | 36.5 | 11.2 | 29.6 | 43.0 | — |
| 22.5 | 6.8 | 79.0 | 32.0 | 30.5 | 36.8 | 11.2 | 29.8 | 43.0 | — |
| 22.0 | 7.3 | — | — | — | — | — | — | — | 76.0 |
| 22.5 | 7.7 | 81.5 | 32.0 | 33.8 | 36.5 | 11.6 | 30.5 | 42.0 | — |
| 22.5 | 8.1 | 83.5 | 31.8 | 35.5 | 36.2 | 11.2 | 30.0 | 42.0 | — |
| | | REGENERATED STRIPPER | | | | | | | |
| 22.5 | 0.2 | 72.0 | 31.8 | 10.8 | 37.5 | 11.4 | 30.5 | 44.0 | — |
| 22.5 | 0.5 | 73.0 | 31.8 | 11.5 | 37.0 | 11.0 | 30.0 | 43.0 | — |
| 22.5 | 0.8 | — | — | — | — | — | — | — | 31.0 |

TABLE VIII
RESPONSE VARIATIONS OBSERVED DURING THE USE OF THE HOLLOW FIBER STRIPPER

| Ambient Temp. °C. | Elapsed Time In Hours | PEAK HEIGHT IN CHART UNITS FOR: | | | | | | |
|---|---|---|---|---|---|---|---|---|
| | | F⁻ | Cl⁻ | NO₂⁻ | PO₄⁻³ | Br⁻ | NO₃⁻ | SO₄⁻² | Ac⁻ |
| 20.5 | 0.3 | 29.0 | 24.3 | 12.0 | 33.8 | 11.2 | 28.8 | 45.2 | — |
| 21.0 | 1.0 | 28.8 | 22.0 | 11.6 | 34.2 | 11.0 | 29.0 | 45.0 | — |
| 21.0 | 1.5 | — | — | — | — | — | — | — | 42.8 |
| 21.0 | 2.0 | 28.8 | 22.2 | 10.5 | 35.6 | 11.5 | 30.5 | 45.5 | — |
| 21.5 | 2.5 | 29.2 | 22.6 | 10.8 | 36.0 | 11.0 | 30.0 | 47.0 | — |
| 21.5 | 3.0 | 29.8 | 22.8 | 10.6 | 36.0 | 11.6 | 31.2 | 46.0 | — |
| 21.5 | 4.2 | — | — | — | — | — | — | — | 43.8 |
| 22.0 | 4.5 | 29.6 | 23.0 | 10.2 | 35.5 | 11.1 | 30.0 | 46.5 | — |
| 22.0 | 5.5 | 30.5 | 23.5 | 9.5 | 36.5 | 11.8 | 32.0 | 47.2 | — |
| 22.0 | 6.0 | — | — | — | — | — | — | — | 44.2 |
| 22.0 | 6.6 | 30.6 | 23.8 | 10.0 | 36.5 | 11.0 | 30.0 | 46.0 | — |
| 22.0 | 7.1 | — | — | — | — | — | — | — | 43.5 |

The data in Table VII indicate a general instrumental upward drift in the response of $Cl^-$, $PO_4^{-3}$, $Br^-$, $NO_3^-$, and $SO_4^{-2}$ not related to exhaustion of the stripper column as evidenced by the response continuity of these ions when the stripper column is regenerated. Acetate and $F^-$ response, measured by peak height, increases with stripper column exhaustion. However, the acetate and $F^-$ responses remain constant when response is measured by peak area using a planimeter. In contrast, both the peak height and peak area response of $NO_2^-$ varies by a factor of about 3 with exhaustion of the stripper column. Nitrite forms nitrous acid in the unexhausted portion of the stripper column and nitrous acid apparently partially reacts with the resin affecting response depending on stripper column exhaustion.

The data in Table VIII indicate that the use of the hollow fiber stripper results in stable response from all of the ions tested. Thus, a very significant advantage of the hollow fiber stripper, with regard to calibration, is that responsiveness is generally not a function of stripper exhaustion but remains reasonably constant with use.

What is claimed is:

1. Apparatus for ion analysis comprising an eluent reservoir, a chromatographic separating means in communication with said reservoir for receiving eluent therefrom, said separating means comprising a separating medium useful for separating ionic species of a sample eluted therethrough using eluent comprising an electrolyte in solution, suppressor means communicating with said separating means for treating effluent eluted therefrom, the suppressor means being comprised of a regenerant, and an ion-exchange membrane partitioning said regenerant from the effluent of the separating means, the membrane being preferentially permeable to ions of the same charge as the exchangeable ions of said membrane, the exchangeable ions of said membrane being in the ion form needed to convert said electrolyte of the eluent to a weakly ionized form, and a detector means suitable for detecting resolved ionic species communicating with the suppressor means for receiving the treated effluent therefrom.

2. The apparatus of claim 1 wherein said membrane is in the form of one or more hollow fibers.

3. The apparatus of claim 2 comprising at least one hollow fiber immersed within a moving stream of said regenerant, the bore of said hollow fiber being in communication with said separating means for receiving the effluent therefrom, said detector means comprising a flow through electrical conductivity cell.

4. The apparatus of claim 3 comprising additional elements of a reservoir of said regenerant, and means to advance said regenerant therefrom to the suppressor means.

5. The apparatus of claim 4 wherein said advancing means is pump means connected to pump regenerant countercurrent to the flow of effluent through the hollow fiber.

6. The apparatus of claim 1 using a strong acid ion-exchange membrane in the hydrogen ion form.

7. The apparatus of claim 6 wherein said membrane comprises a sulfonated polyolefin.

8. The apparatus of claim 7 using a membrane comprising a plurality of hollow fibers, the bores of which communicate with said separating means for receiving the effluent therefrom, said detector means comprising a flow through electrical conductivity cell.

9. The apparatus of claim 1 using a strong base ion-exchange membrane in the hydroxide ion form.

10. The apparatus of claim 9 wherein said membrane comprises an aminated polyolefin.

11. The apparatus of claim 10 using a membrane comprising a plurality of hollow fibers, the bores of which communicate with said separating means for receiving the effluent therefrom, said detector means comprising a flow through conductivity cell.

12. Apparatus for ion analysis comprising an eluent reservoir, a chromatographic separating means in communication with said reservoir for receiving eluent therefrom, said separating means comprising a separating medium useful for separating ionic species of a sample eluted therethrough using eluent comprising an electrolyte in solution, a reservoir of regenerant, an ion-exchange membrane device defining elongated contiguous flow channels communicating with said separating means and reservoir of regenerant, respectively, an ion-exchange membrane which is preferentially permeable to ions of the same charge as the exchangeable ions of said membrane and which comprises partition means between said flow channels, the exchangeable ions of said membrane being in the form needed to convert said electrolyte of the eluent to a weakly ionized form, and a detector means suitable for detecting resolved ionic species communicating with the suppressor means for receiving the treated effluent therefrom.

13. The apparatus of claim 12 wherein said membrane comprises one or more hollow fibers.

14. The apparatus of claim 13 comprising a plurality of hollow fibers adapted to be immersed within a moving stream of regenerant advanced from the reservoir of regenerant by a pump means, the bores of said hollow fibers communicating with said separating means, said detector means comprising a flow through conductivity cell.

15. The apparatus of claim 14 wherein said pump means is connected to pump regenerant countercurrent to the flow of effluent through the hollow fibers.

16. The apparatus of claim 12 using a strong acid ion-exchange membrane in the hydrogen ion form.

17. The apparatus of claim 16 wherein said membrane comprises a sulfonated polyolefin.

18. The apparatus of claim 17 wherein said membrane comprises a polyethylene homopolymer.

19. The apparatus of claim 12 using a strong base ion-exchange membrane in the hydroxide ion form.

20. The apparatus of claim 19 wherein said membrane comprises an aminated polyolefin.

21. The apparatus of claim 20 wherein said membrane comprises a polyethylene homopolymer.

22. Method of ion analysis comprising eluting a sample of predetermined volume and containing ionic species to be quantitated through a separating medium effective to separate ionic species with the aid of an eluent comprising an electrolyte in solution, thereafter contacting the effluent eluting from the separating medium with an ion-exchange membrane permeable to ions of the same charge as the exchangeable ions of said membrane, and which resists permeation therethrough of ions of the opposite charge, and simultaneously contacting the membrane with a regenerant, said membrane forming a permselective partition between the regenerant and said effluent, whereby ions extracted from the effluent at the active ion-exchange sites of the membrane are diffused through the membrane and are exchanged with ions of said regenerant, and are thus diffused ultimately into said regenerant, said exchangeable ions of the ion-exchange membrane being in that form needed to convert said electrolyte of the eluent to a weakly ionized form, said method including the further step of detecting a resolved ionic species contained in said treated effluent.

23. The method of claim 22 wherein said membrane is continuously contacted by a flowing stream of fresh regenerant.

24. The method of claim 23 using a membrane in the form of at least one hollow fiber immersed within a flowing stream containing regenerant.

25. The method of claim 24 using a membrane in the form of a plurality of hollow fibers.

26. The method of claim 25 using the step of routing the effluent of the separating means through the internal bores of said plurality of hollow fibers in a direction countercurrent to the flow of regenerant, said resolved ionic species being detected by measuring the electrical conductivity thereof.

27. The method of claim 26 using fibers comprising a strong acid ion-exchanger in the hydrogen ion form.

28. The method of claim 27 using fibers comprising a sulfonated polyolefin.

29. The method of claim 28 using fibers comprising a polyethylene homopolymer.

30. The method of claim 26 using fibers comprising a strong base ion-exchanger in the hydroxide ion form.

31. The method of claim 30 using fibers comprising an aminated polyolefin.

32. The method of claim 31 using fibers comprising a polyethylene homopolymer.

* * * * *

UNITED STATES PATENT AND TRADEMARK OFFICE
CERTIFICATE OF CORRECTION

PATENT NO. : 4,474,664

DATED : October 2, 1984

INVENTOR(S) : Stevens et al.

Page 1 of 2

It is certified that error appears in the above-identified patent and that said Letters Patent is hereby corrected as shown below:

Column 1, line 24 after "3,920,397" insert --,-- .

Column 4, line 22 delete "pointd" and insert --pointed-- .

Column 6, line 10 after "Mich." insert --)-- .

Column 6, line 32 delete "150" and insert --1/8-- .

Column 7, line 39 delete "then" and insert --than-- .

Column 7, line 64 delete "178" and insert --1/2-- .

Column 8, line 3 delete "178" and insert --1/2-- .

Column 8, line 18 after "in" (second occurrence) delete "the".

Column 9, line 28 delete "na" and insert --Na-- .

Column 9, line 29 delete "meg" and insert --meq-- .

Column 9, line 57 delete "0.1" and insert --0.01-- .

Column 10, line 8 delete "meg" and insert --meq-- .

Column 10, line 34 delete "chromatogaphy" and insert --chromatography-- .

UNITED STATES PATENT AND TRADEMARK OFFICE
CERTIFICATE OF CORRECTION

PATENT NO. : 4,474,664
DATED : October 2, 1984
INVENTOR(S) : Stevens et al

It is certified that error appears in the above-identified patent and that said Letters Patent is hereby corrected as shown below:

Column 13, line 39 delete "Po4" and insert --$PO_4$--.

Signed and Sealed this

Twenty-second Day of October 1985

[SEAL]

Attest:

DONALD J. QUIGG

Attesting Officer

Commissioner of Patents and
Trademarks—Designate